United States Patent [19]

Kormány et al.

[11] 4,032,503

[45] June 28, 1977

[54] PROCESS FOR THE MANUFACTURING OF STYRENE DERIVATIVES, NEW STYRENE DERIVATIVES AND THEIR USE AS OPTICAL BRIGHTENERS

[75] Inventors: Géza Kormány, Allschwil; Guglielmo Kabas, Aesch; Hans Schläpfer; Adolf Emil Siegrist, both of Basel, all of Switzerland

[73] Assignee: Ciba-Geigy Corporation, Ardsley, N.Y.

[22] Filed: Aug. 6, 1975

[21] Appl. No.: 601,884

[30] Foreign Application Priority Data

Aug. 14, 1974 Switzerland ............... 11110/74

[52] U.S. Cl. ............... 260/40 P; 204/158 HE; 260/240 D
[51] Int. Cl.² ............... C08K 5/35
[58] Field of Search ............... 260/240 D, 40 P; 204/158 HE

[56] References Cited

UNITED STATES PATENTS

| | | | |
|---|---|---|---|
| 3,732,221 | 5/1973 | Siegrist et al. | 260/240 D X |
| 3,891,632 | 6/1975 | Fleck et al. | 260/240 D |

FOREIGN PATENTS OR APPLICATIONS 2,025,792  12/1970  Germany ............... 260/240 D

*Primary Examiner*—Sandra M. Person
*Attorney, Agent, or Firm*—Karl F. Jorda; Edward McC. Roberts; Prabodh I. Almaula

[57] ABSTRACT

Process for the manufacture of styrene compounds of the formula

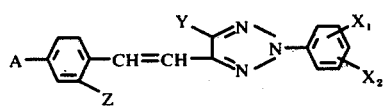

wherein A denotes one of the ring systems

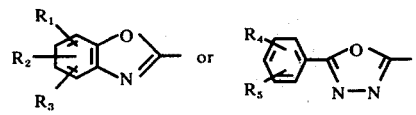

and wherein $R_1$ denotes hydrogen, alkyl with 1 to 8 carbon atoms, cyclohexyl, phenylalkyl with 1 to 3 carbon atoms in the alkyl part, phenyl, alkoxy with 1 to 4 carbon atoms, or chlorine, or, conjointly with $R_2$, denotes alkylene with 3 or 4 carbon atoms, $R_2$ denotes hydrogen or alkyl with 1 to 4 carbon atoms or, conjointly with $R_1$, denotes alkylene with 3 or 4 carbon atoms, $R_3$ denotes hydrogen or methyl, $R_4$ denotes hydrogen, m-methyl, alkyl with 2 to 8 carbon atoms, phenyl, alkoxy with 1 to 4 carbon atoms, or chlorine, or, conjointly with $R_5$, denotes a fused benzene ring, $R_5$ denotes hydrogen or chlorine or, conjointly with $R_4$, denotes a fused benzene ring, $X_1$ denotes hydrogen, alkyl with 2 to 4 carbon atoms, alkoxy with 1 to 4 carbon atoms or chlorine, $X_2$ denotes hydrogen or chlorine, Y denotes hydrogen, chlorine, alkyl with 1 to 4 carbon atoms or phenyl and Z denotes hydrogen or chlorine, which is characterized in that a methyl compound of the formula

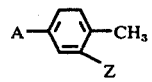

is reacted with a Schiff's base of the formula

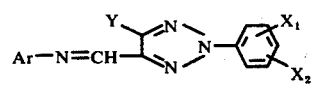

wherein Ar denotes an aromatic radical, in dimethylformamide in the presence of a strongly basic alkali metal compound, the reaction mixture being irradiated, at least initially, with UV light.

13 Claims, No Drawings

PROCESS FOR THE MANUFACTURING OF STYRENE DERIVATIVES, NEW STYRENE DERIVATIVES AND THEIR USE AS OPTICAL BRIGHTENERS

The present invention relates to a new process for the manufacture of styrene compounds, which are substituted by heterocyclic radicals containing ring nitrogen atoms, and to new styrene derivatives and their use as optical brighteners for high molecular organic materials, especially synthetic organic materials, preferably polyester.

It is already known that styrene compounds which are substituted by heterocyclic radicals containing ring nitrogen atoms can be manufactured by means of the anil synthesis. However, only very moderate yields are obtained according to the known procedure since, due to the side reactions (splitting of the heterocyclic radicals containing ring nitrogen atoms) which readily occur, the reaction can only be carried out under mild conditions.

It has now been found, that, surprisingly, a considerable increase in the yields can be achieved when the reaction mixture is irradiated with ultraviolet light.

Accordingly, the invention relates to a process for the manufacture of styrene compounds of the formula

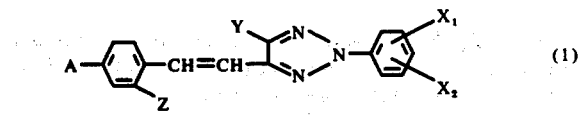 (1)

wherein A denotes one of the ring systems

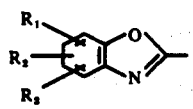 (1a)

or

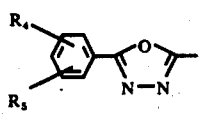 (1b)

and wherein $R_1$ denotes hydrogen, alkyl with 1 to 8 carbon atoms, cyclohexyl, phenylalkyl with 1 to 2 carbon atoms in the alkyl part, phenyl, alkoxy with 1 to 4 carbon atoms, or chlorine, or, conjointly with $R_2$, denotes alkylene with 3 or 4 carbon atoms, $R_2$ denotes hydrogen or alkyl with 1 to 4 carbon atoms or, conjointly with $R_1$, denotes alkylene with 3 or 4 carbon atoms, $R_3$ denotes hydrogen or methyl, $R_4$ denotes hydrogen m-methyl, alkyl with 2 to 8 carbon atoms, phenyl, alkoxy with 1 to 4 carbon atoms, or chlorine, or, conjointly with $R_5$, denotes a fused benzene ring, $R_5$ denotes hydrogen or chlorine or, conjointly with $R_4$, denotes a fused benzene ring, $X_1$ denotes hydrogen, alkyl with 2 to 4 carbon atoms, alkoxy with 1 to 4 carbon atoms or chlorine, $X_2$ denotes hydrogen or chlorine, Y denotes hydrogen, chlorine alkyl with 1 to 4 carbon atoms or phenyl and Z denotes hydrogen or chlorine, which is characterised in that a methyl compound of the formula

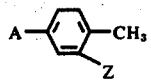 (2)

is reacted with a Schiff's base of the formula

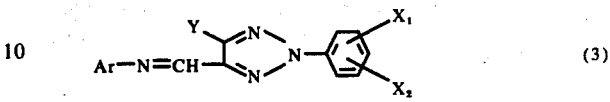 (3)

wherein Ar denotes an aromatic radical, in dimethylformamide in the presence of a strongly basic alkali metal compound, the reaction mixture being irradiated, at least initially, with UV light.

The irradiation, according to the invention, with UV light is effected by means of a source which is located either outside or inside the reaction vessel. In general, the irradiation with UV light is required only in order to start the reaction and not for all the time until the reaction between the reactants has gone to completion. Therefore, an irradiation time of a few minutes is usually sufficient. Preferably, UV light with a wavelength of above 300 nm is used.

In general, the symbol Ar represents an optionally substituted naphthyl or, in particular, phenyl radical. Preferably, Ar represents the radical of the formula

 (4)

wherein k denotes hydrogen or chlorine.

The strongly basic alkali compound used is generally such a compound of the formula

 (5)

$MOC_{n-1}H_{2n-1}$ wherein M denotes potassium or sodium and n denotes an integer from 1 to 6.

Examples of compounds of the formula (5) which may be mentioned are sodium methylate, potassium tertiary butylate, sodium hydroxide and potassium hydroxide.

In the case of alcoholates, the reaction must be carried out in a virtually anhydrous medium, whilst in the case of the hydroxides, water contents of up to 25% are permissible. In the case of potassium hydroxide, which is preferably to be used, a water content of up to about 15% has proved suitable.

Appropriately, the compound containing methyl groups and the Schiff's base are reacted in equivalent amounts so that neither component is present in a substantial excess. Advantageously, at least the equivalent amount of the alkali metal compound is used, that is to say at least 1 mol of alkali metal compound per mol of Schiff's base. When potassium hydroxide is used, two to eight times the equivalent amount are preferably employed.

The reaction according to the invention can be carried out at temperatures in the range between about 10° and 40° C. If potassium hydroxide is used for the reaction, the reaction generally already takes place at room temperature, in which case it is not necessary to supply heat from outside. When other alkali metal compounds are used the reaction must be carried out at elevated temperatures, depending on the base strength of these compounds. However, a reaction temperature which is as low as possible is desirable, since at higher temperatures side reactions, such as, for example, opening of the ring, can occur.

The end products can be worked up from the reaction mixture according to customary methods which are in themselves known.

Within the above framework, a process to be singled out is that for the manufacture of styrene compounds of the formula

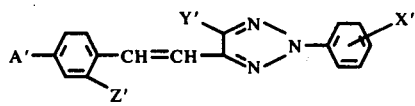

wherein A' denotes one of the ring systems

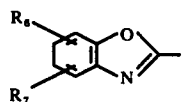

or

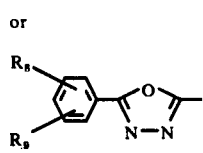

and wherein $R_6$ denotes hydrogen, alkyl with 1 to 4 carbon atoms, cyclohexyl, benzyl, α,α-dimethylbenzyl, methoxy, phenyl or chlorine, $R_7$ denotes hydrogen or methyl, $R_8$ denotes hydrogen, m-methyl, alkyl with 2 to 4 carbon atoms, phenyl, methoxy or chlorine or, conjointly with $R_9$, denotes a fused benzene ring, $R_9$ denotes hydrogen or, conjointly with $R_8$, denotes a fused benzene ring, X' denotes hydrogen, alkyl with 2 to 4 carbon atoms, methoxy or chlorine, Y' denotes hydrogen, methyl or phenyl and Z' denotes hydrogen or chlorine, characterised in that a methyl compound of the formula

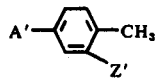

is reacted with a Schiff's base of the formula

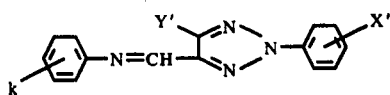

wherein k denotes hydrogen or chlorine, in dimethylformamide in the presence of an alkali metal compound of the formula (5), the reaction mixture initially being irradiated with UV light of wavelengths of above 300 nm.

Particular technical interest attaches to the manufacture of the compounds of the formula

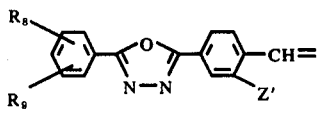

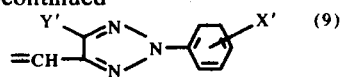

wherein $R_8$, $R_9$, Z', Y' and X' have the abovementioned meaning, for which purpose a compound of the formula

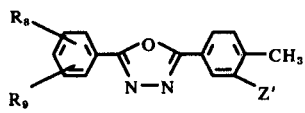

is reacted with a compound of the formula (8).

Preferably, potassium hydroxide is used as the alkali metal compound in each case and the reaction is carried out at a temperature of 10° to 40° C.

Amongst the end products mentioned above, those of the formula

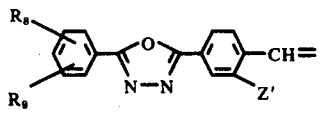

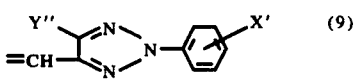

wherein $R_8$, $R_9$, X' and Z' have the abovementioned meaning and Y" denotes methyl or phenyl, are new; they have unexpected brightener properties.

Compounds of particular interest are those of the formula

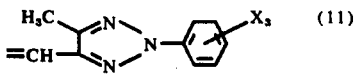

wherein $R_{10}$ denotes chlorine, methoxy, tert.-butyl or phenyl and $X_3$ denotes hydrogen, chlorine or p-methoxy.

Individual compounds to be singled out are those of the formulae

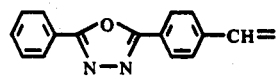

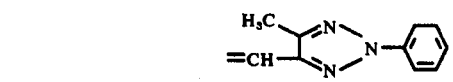

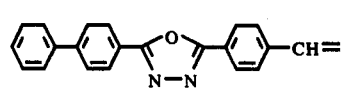

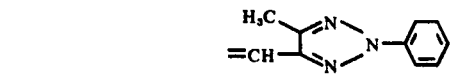

and

-continued

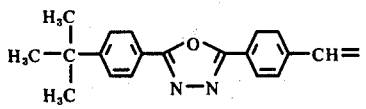

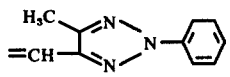    (14)

The compounds, defined above, of the formula (1) and expecially the new compounds of the formula (9) show a more or less pronounced fluorescence in the dissolved or finely divided state. They can be used for the optical brightening of the most diverse synthetic, semi-synthetic or natural organic material or substances which contain such organic materials.

The following groups of organic materials, where optical brightening thereof is relevant, may be mentioned as examples of the above, without the survey given below being intended to express any restriction thereto:

I. Synthetic organic high molecular materials:

a. Polymerisation products based on organic compounds containing at least one polymerisable carbon-carbon double bond, that is to say their homopolymers or copolymers as well as their after-treatment products such as, for example, cross-linking, grafting or degradation products, polymer blends or products obtained by modification of reactive groups, for example polymers based on $\alpha,\beta$-unsaturated carboxylic acids or derivatives of such carboxylic acids, especially on acrylic compounds (such as, for example, acrylic esters, acrylic acid, acrylonitrile, acrylamides and their derivatives or their methacryl analogues), on olefine hydrocarbons (such as, for example, ethylene, proplyene, styrenes or dienes and also so-called ABS polymers), and polymers based on vinyl and vinylidene compounds (such as, for example, vinyl chloride, vinyl alcohol and vinylidene chloride), b. Polymerisation products such as are obtainable by ring opening, for example polyamides of the polycaprolactam type, and also polymers which are obtainable both via polyaddition and via polycondensation, such as polyethers or polyacetals.

c. Polycondensation products or precondensates based on bifunctional or polyfunctional compounds possessing condensable groups, their homocondensation and co-condensation product, and after-treatment products, such as, for example, polyesters, especially saturated (for example ethylene glycol terephthalic acid polyester) or unsaturated (for example maleic acid-dialcohol polycondensates as well as their cross-linking products with copolymerisable vinyl monomers), unbranched and branched (also including those based on polyhydric alchohols, such as, for example, alkyd resins) polyesters, polyamides (for example hexamethylenediamine adipate), maleate resins, melamine resins, their precondensates and analogues, polycarbonates and silicones, d. Polyaddition products such as polyurethanes (crosslinked and non-crosslinked) and epoxide resins.

II. Semi-synthetic organic materials, for example cellulose esters of varying degrees of esterification (so-called 2½-acetate or triacetate) or cellulose ethers, regenerated cellulose (viscose or cuprammonium cellulose), or their after-treatment products, and casein plastics.

III. Natural organic materials of animal or vegetable origin, for example based on cellulose or proteins, such as cotton, wool, linen, silk, natural lacquer resins, starch and casein.

The organic materials to be optically brightened can be in the most diverse states of processing (raw materials, semi-finished goods or finished goods). On the other hand, they can be in the form of structures of the most diverse shapes, say for example predominantly three-dimensional bodies such as sheets, profiles, injection mouldings, various machined articles, chips, granules or foams, and also as predominantly two-dimensional bodies such as films, foils, lacquers, coatings, impregnations and coverings, or as predominantly one-dimensional bodies such as filaments, fibres, flocks and wires. The said materials can, on the other hand, also be in an unshaped state, in the most diverse homogeneous or inhomogeneous forms of division, such as, for example, in the form of powders, solutions, emulsions, dispersions, latices, pastes or waxes.

Fibre materials can, for example, be in the form of endless filaments (stretched or unstretched), staple fibres, flocks, hanks, textile filaments, yarns, threads, fibre fleeces, felts, waddings, flocked structures or woven textile fabrics, textile laminates, knitted fabrics and papers, cardboards or paper compositions.

The compounds to be used according to the invention are of importance, inter alia, for the treatment of organic textile materials, especially woven textile fabrics. Where fibres, which can be in the form of staple fibres or endless filaments or in the form of hanks, woven fabrics, knitted fabrics, fleeces, flocked substrates or laminates, are to be optically brightened according to the invention, this is advantageously effected in an agueous medium, wherein the compounds in question are present in a finely divided form (suspensions, so-called microdispersions or possible solutions). If desired, dispersing agents, stabilisers, wetting agents and further auxiliaries can be added during the treatment.

Depending on the type of brightener compound used, it may prove advantageous to carry out the treatment in a neutral or alkaline or acid bath. The treatment is usually carried out at temperatures of about 20° to 140° C, for example at the boiling point of the bath or near it (about 90° C). Solutions or emulsions in organic solvents can also be used for the finishing, according to the invention, of textile substrates, as is practised in the dyeing trade in so-called solvent dyeing (pad-thermofix application, or exhaustion dyeing process in dyeing machines).

The optical brighteners according to the present invention can further be added to, or incorporated in, the materials before or during their shaping. Thus they can, for example, be added to the compression moulding composition or injection moulding composition during the manufacture of films, sheets (for example, hot milling into polyvinyl chloride) or mouldings.

Where fully synthetic or semi-synthetic organic materials are being shaped by spinning processes or via spinning compositions, the optical brighteners can be applied in accordance with the following processes:

Addition to the starting substances (for example monomers) or intermediates (for example precondensates or prepolymers), that is to say before or during the polymerisation, polycondensation or polyaddition, Powdering onto polymer chips or granules for spinning compositions, Bath dyeing of polymer chips or granules for spinning compositions, and application to the tow before stretching.

The optical brighteners of the formula (1) and, in particular, the new optical brighteners according to formula (9) can, for example, also be employed in the following use forms:

a. Mixed with dyestuffs (shading) or pigments (coloured pigments or especially, for example, white pigments), or as an additive to dye baths, printing pastes, discharge pastes or reserve pastes, and furthermore for the after-treatment of dyeing, prints or discharge prints.

b. Mixed with so-called "carriers", wetting agents, plasticisers, swelling agents, anti-oxidants, light protection agents, heat stabilisers and chemical bleaching agents (chlorite bleach or bleaching bath additives).

c. Mixed with crosslinking agents or finishing agents (for example starch or synthetic finishes), and in combination with the most diverse textile finishing processes, especially synthetic resin finishes (for example creaseproof finishes such as "wash-and "wear", "permanent-press" or "no-iron"), as well as flameproof finishes, soft handle finishes, anti-soiling finishes or anti-static finishes, or antimicrobial finishes.

d. Incorporation of the optical brighteners into polymeric carriers (polymerisation, polycondensation or polyaddition products), in a dissolved or dispersed form, for use, for example, in coating agents, impregnating agents or binders (solutions, dispersions and emulsions) for textiles, fleeces paper and leather.

e. As additives to so-called "master batches".

f. As additives to the most diverse industrial products in order to render these more marketable (for example improving the appearance of soaps, detergents, pigments), g. In combination with other optically brightening substances, h. In spinning bath preparations, that is to say as additives to spinning baths such as are used for improving the slip for the further processing of synthetic fibres, or from a special bath before the stretching of the fibre.

i. As scintillators for various purposes of a photographic nature, such as, for example, for electrophotographic reproduction or supersensitisation, and for the optical brightening of photographic layers, optionally in combination with white pigments such as, for example, $TiO_2$.

k. Depending in each case on the substitution, as laser dyestuffs.

If the brightening process is combined with textile treatment methods or finishing methods, the combined treatment can in many cases advantageously be carried out with the aid of appropriate stable preparations, which contain the optically brightening compounds in such concentration that the desired brightening effect is achieved.

In certain cases, the brighteners are made fully effective by an after-treatment. This can, for example, represent a chemical treatment (for example acid treatment), a thermal treatment (for example heat) or a combined chemical/thermal treatment. Thus, for example, the appropriate procedure to follow in optically brightening a series of fibre substrates, for example of polyester fibres, with the brighteners according to the invention is to impregnate these fibres with the aqueous dispersions (or optionally also solutions) of the brighteners at temperatures below 75° C, for example at room temperature, and to subject them to a dry heat treatment at temperatures above 100° C, it being generally advisable additionally to dry the fibre material beforehand at a moderately elevated temperature, for example at not less than 60° and up to about 130° C. The heat treatment in the dry state is then advantageously carried out at temperatures between 120° and 255° C, for example by heating in a drying chamber, by ironing within the specified temperature range or by treatment with dry, superheated steam. The drying and dry heat treatment can also be carried out in immediate succession or be combined in a single process stage.

The amount of the optical brighteners to be used, relative to the material to be optically brightened, can vary within wide limits. A distinct and durable effect is already achievable with very small amounts, in certain cases, for example, amounts of 0.0001 percent by weight. However, amounts of up to about 0.8 percent by weight and optionally of up to about 2 percent by weight can also be employed. For most practical purposes, amounts between 0.0005 and 0.5 percent by weight are of preferred interest.

The brightening agents defined above are also particularly suitable for use as additives for wash liquors or industrial and domestic washing agents, to which they can be added in various ways. They are appropriately added to wash liquors in the form of their solutions in water or organic solvents or in a finely divided form, as aqueous dispersions. They are advantageously added to domestic or industrial washing agents in any stage of the manufacturing process of the washing agents, for example to the so-called "slurry"before spray-drying, to the washing powder, or during the preparation of liquid washing agent combinations. They can be added either in the form of a solution or dispersion in water or other solvents or, without auxiliaries, as a dry brightening powder. For example, the brightening agents can be mixed, kneaded or ground with the detergent substances and, in this form, admixed to the finishing washing powder. However, they can also be sprayed in a dissolved or predispersed form onto the finished washing agent.

Possible washing agents are the known mixtures of detergent substances such as, for example, soap in the form of chips and powders, synthetics, soluble salts of sulphonic acid half-esters of higher fatty alcohols, arylsulphonic acids with higher and/or multiple alkyl substituents, sulphocarboxylic acid esters of medium to higher alcohols, fatty acid acylaminoalkyl or acylaminoaryl-glycerol sulphonates, phosphoric acid esters of fatty alcohols and the like. Possible so-called "builders" which can be used are, for example, alkali metal polyphosphates and polymetaphosphates, alkali metal pyrophosphates, alkali metal salts of carboxymethylcellulose and other "soil redeposition inhibitors", and also alkali metal silicates, alkali metal carbonates, alkali metal borates, alkali metal perborates, nitrilotriacetic acid, ethylenediaminotetraacetic acid, and foam stabilisers such as alkanolamides of higher fatty acids. The washing agents can further contain, for example: antistatic agents, skin protection agents which restore fat, such as lanolin, enzymes, antimicrobial agents, perfumes and dyestuffs.

The new optical brighteners have the particular advantage that they are also active in the presence of active chlorine donors such as, for example, hypochlorite, and can be used without significant loss of the effects in wash liquors containing non-ionic washing agents, for example alkylphenol polyglycol ethers.

The optical brightening agents are added in amounts of 0.005–1% or more, relative to the weight of the liquid or pulverulent finished washing agent. Wash liquors which contain the indicated amounts of the optical brighteners claimed impart a brilliant appearance in daylight when used to wash textiles of cellulose fibres, polyamide fibres, cellelose fibres with a high quality finish, polyester fibres, wool and the like.

The washing treatment is carried out as follows, for example:

The textiles indicated are treated for 1 to 30 minutes at 20° to 100° C in a wash liquor which contains 1 to 10 g/kg of a built-up composite washing agent and 0.05 to 1%, relative to the weight of the washing agent, of the brightening agents defined above. The liquor ratio can be 1:3 to 1:50. After washing, the textiles are rinsed and dried in the usual manner. The wash liquors can contain 0.2 g/l of active chlorine (for example as hypochlorite) or 0.1 to 2 g/l of sodium perborate as a bleaching additive.

In the examples the parts, unless otherwise stated, are always parts by weight and the percentages are always percentages by weight. Unless otherwise noted, melting points and boiling points are uncorrected.

EXAMPLE 1

3.49 g (0.0166 mol) of 2-(p-tolyl)-benzoxazole of the formula

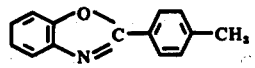 (101)

and 4.95 g (0.0166 mol) of the Schiff's base, obtained from 2-phenyl-4-formyl-5-methyl-2H-1,2,3-triazole and p-chloroaniline, of the formula

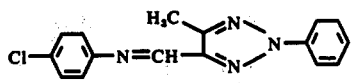 (102)

(melting point: 95.5° to 96° C) and 4.16 g (~ 0.066 mol) of powdered potassium hydroxide with a water content of about 10% are stirred in 80 ml of dimethylformamide for one hour at 20° to 25° C, under nitrogen. During the first 10 minutes of the reaction, the reaction mixture is irradiated with UV light of wavelengths of above 300 nm. The colour of the reaction mixture gradually changes from yellow via violet-brown to red-brown. Thereafter, 320 ml of methanol are added and the mixture is cooled to −10° C. The product which has precipitated is filtered off, washed by covering several times with a total of 50 ml of methanol and dried. 4.1 g (corresponding to 65.1% of theory) of β-(2-phenyl-5-methyl-2H-1,2,3-triazol-4-yl)-4-(benzoxazol-2-yl)-styrene of the formula

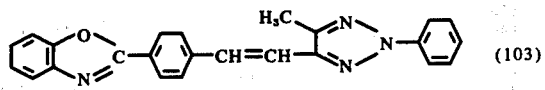 (103)

are obtained as a pale beige-yellow powder of melting point 201° to 202° C. After recrystallising twice from toluene/ethanol (1:2) (bleaching earth), 3.7 g (corresponding to 58.7% of theory) of small, pale green, shiny needles, which melt at 202° to 203° C, are obtained.

Analysis: $C_{24}H_{18}N_4O$ (378.42) Calculated: C 76.17 H 4.79 N 14.81; Found: C 76.19 H 4.95 N 14.87.

If the reaction is carried out without exposing the mixture to UV light, the compound (103) is obtained in a yield of only 28.6% of theory (1.8 g), the melting point being 200° to 201° C. After recrystallising twice from toluene/ethanol (1:2), 25.9% of theory (1.63 g) of analytically pure product (103) of melting point 202° to 203° C are obtained.

The compounds of the formula

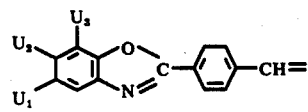

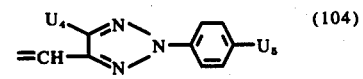 (104)

which are listed in Table I which follows, can be prepared analogously using UV light:

Table I

| No. | $U_1$ | $U_2$ | $U_3$ | $U_4$ | $U_5$ | Melting point ° C |
|-----|-------|-------|-------|-------|-------|-------------------|
| 105 | H | H | H | H | H | 230 – 231 |
| 106 | —CH$_3$ | H | H | H | H | 231 – 232 |
| 107 | H | —CH$_3$ | H | H | H | 210 – 211 |
| 108 | —CH$_3$ | —CH$_3$ | H | H | H | 256 – 257 |
| 109 | —CH$_3$ | H | H | —CH$_3$ | H | 186.5 – 187 |
| 110 | H | —CH$_3$ | H | —CH$_3$ | H | 204 – 205 |
| 111 | —CH$_3$ | —CH$_3$ | H | —CH$_3$ | H | 224 – 225 |
| 112 | —CH$_2$CH$_2$CH$_3$ | H | H | H | H | 214 – 215 |
| 113 | —CH$_2$CH$_2$CH$_3$ | H | H | —CH$_3$ | H | 156 – 156.5 |
| 114 | —CH(CH$_3$)$_2$ | H | H | H | H | 169.5 – 170 |
| 115 | —CH(CH$_3$)$_2$ | H | H | —CH$_3$ | H | 154.5 – 155 |
| 116 | —C(CH$_3$)$_3$ | H | H | H | H | 177 – 177.5 |
| 117 | —C(CH$_3$)$_3$ | H | —CH$_3$ | —CH$_3$ | H | 164 – 164.5 |
| 118 | —CH$_2$C$_6$H$_5$ | H | H | H | H | 216 – 217 |
| 119 | —CH$_2$C$_6$H$_5$ | H | H | —CH$_3$ | H | 179 – 179.5 |
| 120 | —C(CH$_3$)$_2$C$_6$H$_5$ | H | H | H | H | 158 – 158.5 |
| 121 | —Cyclohexyl | H | H | H | H | 221 – 222 |
| 122 | —C$_6$H$_5$ | H | H | H | H | 238 – 239 |
| 123 | H | —C$_6$H$_5$ | H | H | H | 222 – 223 |
| 124 | —C$_6$H$_5$ | H | H | —CH$_3$ | H | 182.5 – 183 |
| 125 | H | —C$_6$H$_5$ | H | —CH$_3$ | H | 189 – 189.5 |
| 126 | —OCH$_3$ | H | H | H | H | 207 – 208 |
| 127 | H | H | H | H | —OCH$_3$ | 200 – 201 |
| 128 | —CH$_3$ | H | H | H | —OCH$_3$ | 196.5 – 197 |
| 129 | H | —CH$_3$ | H | H | —OCH$_3$ | 191.5 – 192 |

Table I-continued

| No. | U₁ | U₂ | U₃ | U₄ | U₅ | Melting point °C |
|---|---|---|---|---|---|---|
| 130 | —Cl | H | H | H | H | 225 – 226 |
| 131 | —Cl | H | H | —CH₃ | H | 218 – 219 |
| 132 | —C₂H₅ | H | H | H | —Cl | 223 – 224 |
| 133 | —CH₂C₆H₅ | H | H | H | —Cl | 234 – 235 |
| 134 | H | —C₆H₅ | H | H | —Cl | 263 – 264 |
| 135 | —CH₂—CH₂—CH₂— | | H | H | H | 223 – 224 |
| 136 | —CH₂—CH₂—CH₂— | | H | —CH₃ | H | 226 – 227 |
| 137 | H | H | H | —CH₃ | —Cl | 237 – 238 |
| 138 | —CH₃ | H | H | —CH₃ | —Cl | 234 – 235 |
| 139 | H | —CH₃ | H | —CH₃ | —Cl | 225 – 226 |
| 140 | —CH₃ | —CH₃ | H | —CH₃ | —Cl | 249 – 250 |
| 141 | —C₆H₅ | H | H | —CH₃ | —Cl | 230 – 231 |
| 142 | H | —C₆H₅ | H | —CH₃ | —Cl | 246 – 247 |
| 143 | H | H | H | —C₆H₅ | H | 199 – 199.5 |
| 144 | —CH₃ | H | H | —C₆H₅ | H | 214 – 215 |
| 145 | H | —CH₃ | H | —C₆H₅ | H | 202 – 203 |
| 146 | —CH₃ | —CH₃ | H | —C₆H₅ | H | 244 – 245 |
| 147 | —C₆H₅ | H | H | —C₆H₅ | H | 215 – 216 |
| 148 | H | —C₆H₅ | H | —C₆H₅ | H | 220 – 221 |
| 149 | H | H | H | —C₆H₅ | —Cl | 250 – 251 |
| 150 | —CH₃ | H | H | —C₆H₅ | —Cl | 247 – 248 |
| 151 | H | —CH₃ | H | —C₆H₅ | —Cl | 219 – 220 |

EXAMPLE 2

3.94 g (0.0166 mol) of 2-(p-tolyl)-5-phenyl-1,3,4-oxadiazole of the formula

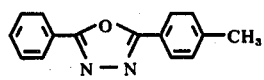
(152)

and 4.74 g (0.0166 mol) of the Schiff's base, obtained from 2-phenyl-4-formyl-2H-1,2,3-triazole and p-chloroaniline, of the formula

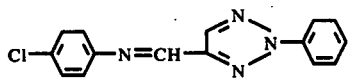
(153)

(melting point: 117° to 117.5° C) and 4.16 g (~0.066 mol) of powdered potassium hydroxide with a water content of about 10% are stirred in 80 ml of dimethylformamide for one hour at 20° to 25° C, under nitrogen. During the first 10 minutes of the reaction, the reaction mixture is irradiated with UV light of wavelengths above 300 nm. The colour of the reaction mixture gradually changes from pale yellow via brown to red-violet. 320 ml of methanol are then added and the mixture is cooled to −10° C. The product which has precipitated is filtered off, washed by covering several times with a total of 50 ml of methanol and dried. 5.0 g (corresponding to 76.9% of theory) of β-(2-phenyl-2H-1,2,3-triazol-4-yl)-4-(5-phenyl-1,3,4-oxadiazol-2-yl)-styrene of the formula

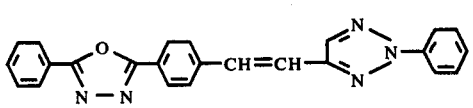
(154)

are obtained as small, pale yellow, fine needles of melting point 222° to 223° C. After recrystallising twice from toluene (bleaching earth), 4.4 g (corresponding to 67.7% of theory) of small colourless matted needles of melting point 224° to 225° C are obtained.

Analysis: C₂₄H₁₇N₅O (391.42)
Calculated: C 73.64 H 4.38 N 17.89; Found: C 73.46 H 4.36 N 17.82.

The compounds of the formula

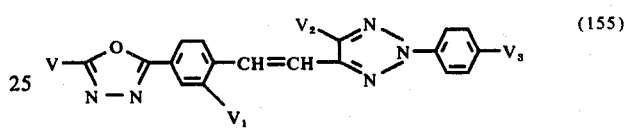
(155)

which are listed in Table II which follows can be prepared analogously.

Table II

| No. | 10 V | V₁ | V₂ | V₃ | Melting point °C |
|---|---|---|---|---|---|
| 156 | m-C₆H₄CH₃ | H | H | H | 223 – 224 |
| 157 | p-C₆H₄(CH₃)₃ | H | H | H | 198 – 198.5 |
| 158 | m-C₆H₄OCH₃ | H | H | H | 214 – 215 |
| 159 | p-C₆H₄OCH₃ | H | H | H | 225 – 226 |
| 160 | p-C₆H₄Cl | H | H | H | 233 – 234 |
| 161 | p-C₆H₄C₆H₅ | H | H | H | 250 – 251 |
| 162 | Naphthyl-(1) | H | H | H | 251 – 252 |
| 163 | —C₆H₅ | H | —CH₃ | H | 216 – 217 |
| 164 | m-C₆H₄CH₃ | H | —CH₃ | H | 181 – 181.5 |
| 165 | p-C₆H₄C(CH₃)₃ | H | —CH₃ | H | 192.5 – 193 |
| 166 | m-C₆H₄OCH₃ | H | —CH₃ | H | 183.5 – 184 |
| 167 | p-C₆H₄OCH₃ | H | —CH₃ | H | 213 – 214 |
| 168 | p-C₆H₄Cl | H | —CH₃ | H | 218 – 219 |
| 169 | p-C₆H₄C₆H₅ | H | —CH₃ | H | 203 – 204 |
| 170 | Naphthyl-(1) | H | —CH₃ | H | 192 – 192.5 |
| 171 | —C₆H₅ | H | —CH₃ | —Cl | 262 – 263 |
| 172 | p-C₆H₄C₆H₅ | H | —CH₃ | —Cl | 234 – 235 |
| 173 | —C₆H₅ | H | —C₆H₅ | H | 228 – 229 |
| 174 | p-C₆H₄C₆H₅ | H | —C₆H₅ | H | 233 – 234 |
| 175 | p-C₆H₄C₆H₅ | H | —C₆H₅ | —Cl | 240 – 241 |
| 176 | —C₆H₅ | —Cl | H | H | 228 – 229 |
| 177 | —C₆H₅ | —Cl | H | —Cl | 241 – 242 |
| 178 | —C₆H₅ | —Cl | —CH₃ | H | 216 – 217 |
| 179 | —C₆H₅ | —Cl | —CH₃ | —Cl | 249 – 250 |
| 180 | —C₆H₅ | H | H | —OCH₃ | 207 – 208 |

Manufacture of the intermediate products

A. 4-Formyl-2-(4′-methoxyphenyl)-1,2,3-triazole 24.6 g of p-anisidine, 70 ml of water and 52 g of concentrated hydrochloric acid are mixed and the mixture is stirred for 30 minutes at 70° C, after which the solution is cooled from outside to 0° – 5° C and a solution of 14 g of sodium nitrite in 40 ml of water is added. The mixture is stirred for 30 minutes at 0° to 5° C and the excess nitrite is then destroyed with dilute aqueous sulphamic acid. The diazo mixture thus obtained is then introduced into a solution of 16 g of malonic dialdehyde in 100 ml of water (prepared by hydrochloric acid-catalysed saponification of 48.5 g of tetraethoxypropane) at 5° C. The pH is kept at 4.2 – 4.5 by adding sodium acetate. The batch is stirred overnight at 0° to 5° C and then filtered and the filter cake is washed with water. After drying, 37.3 g of crude 4-methoxyphenylazo-malonic dialdehyde of melting point 127° – 129° C are obtained.

A suspension of 36 g of this product in 100 ml of ethanol is mixed with a solution of 53.2 g of sodium acetate dihydrate in 80 ml of water and a solution of 25.4 g of hydroxylamine hydrochloride in 35 ml of water and the mixture is stirred for 2 hours at 60° C. After cooling, the batch is filtered and the filter cake is washed well with water. After drying, 35.4 g of the 4-methoxyphenylhydrazone of diisonitrosoacetone, of melting point 165° – 166°·C, are obtained.

47.2 g of the 4-methoxyphenylhydrazone of diisonitrosoacetone are dissolved in 60 ml of dimethylformamide and the solution is treated at 10° – 15° C with 20.2 g of triethylamine and 20.4 g of acetic anhydride. The dark brown mixture is stirred for 7 hours at 80° C and then poured into 500 ml of water, the mixture is filtered and the filter cake is then washed with water. The filter cake is now suspended in 150 ml of water, after which the pH is brought to 13 by adding sodium hydroxide solution. The suspension is now clarified, the filtrate is neutralised with hydrochloric acid and the product which has precipitated is filtered off and washed with water. After recrystallisation of the dry filter cake from ethanol, 22 g of 4-aldoximino-2-(4'-methoxyphenyl)-1,2,3-triazole of melting point 124° – 126° C are obtained.

22 g of 4-aldoximino-2-(4'-methoxyphenyl)-1,2,3-triazole are dissolved, at 70° C, in 150 ml of 50% strength aqueous ethanol, the solution is mixed with 29.1 g of sodium metabisulphite and the mixture is stirred for 3 hours at 80° C, after which the ethanol is distilled off. After cooling, the brown reaction mixture is clarified and the filtrate is acidified with hydrochloric acid, the crude aldehyde precipitating out. After recrystallisation of the dry aldehyde from n-hexane, 16 g of 4-formyl-2-(4'-methoxyphenyl)-1,2,3-triazole of melting point 103° – 104° C are obtained.

4-Formyl-2-(4'chlorophenyl)-1,2,3-triazole, which after recrystallisation from n-hexane has a melting point of 118° – 120° C, is obtained in a similar manner using p-chloroaniline.

B. 4-Formyl-2,5-diphenyl-1,2,3-triazole 2,5-Diphenyl-1,2,3-triazole-carboxylic acid ethyl ester was prepared analogously to the process described in Swiss Patent Specification 552,603, starting from 2-phenylazobenzoylacetic acid ethyl ester and ammonium acetate, in the presence of copper-(II) chloride dihydrate, in ethanol.

The ester thus obtained was saponified, without further purification, with sodium hydroxide solution, by which means 2,5-diphenyl-1,2,3-triazole-4-carboxylic acid is obtained; after recrystallisation from chlorobenzene it has a melting point of 211° – 212° C.

120 g of this acid, 400 ml of benzene, 0.5 g of dimethylformamide and 70 g of thionyl chloride are mixed and kept at 80° C overnight. After distilling off the readily volatile fractions, 2,5-diphenyl-1,2,3-triazole-4-carboxylic acid chloride distils at 174° – 176°/0.15 mm Hg; 117 g of acid chloride of melting point 112° – 113° C are obtained.

A uniform stream of hydrogen is passed through a suspension consisting of 28.3 g of 2,5-diphenyl-1,2,3-triazole-4-carboxylic acid chloride and 2.1 g of a catalyst (5% palladium-on-barium sulphate). The temperature of the suspension is brought to 95° – 100° C and the suspension is stirred at this temperature until evolution of hydrogen chloride ceases, which is the case after 2 to 3 hours. The catalyst is then filtered off and washed with 100 ml of xylene and the filtrate is evaporated. After recrystallisation of the residue from ethanol, 23.4 g of 2,5-diphenyl-4-formyl-1,2,3-triazole of melting point 93° – 94° C are obtained.

In a similar manner, 2-(4'-chlorophenyl)-4-formyl-5-phenyl-1,2,3-triazole of melting point 137° – 138° C is obtained using 2-(4'-chlorophenylazo)-benzoylacetic acid ethyl ester and 2-(4'chlorophenyl)-4-formyl-5-methyl-1,2,3-triazole of melting point 110° – 111° C is obtained using 2-(4'-chlorophenylazo)-acetoacetic acid ethyl ester.

C. Schiff's bases

The Schiff's bases of the formula

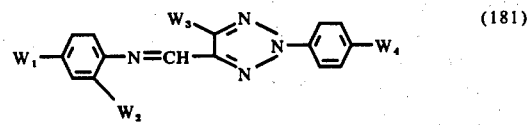

(181)

used in Examples 1 and 2 can be prepared by melting the corresponding aldehydes together with o-chloroaniline and p-chloroaniline respectively (10% excess) for 30 minutes at 180° to 185° C, under a nitrogen atmosphere and whilst distilling off the water formed.

The Schiff's bases of the formula (181) which are indicated in Table III are obtained in an analogous manner.

Table III

| No. | $W_1$ | $W_2$ | $W_3$ | $W_4$ | Melting point ° C |
|---|---|---|---|---|---|
| 153 | —Cl | H | H | H | 117 – 117.5 |
| 102 | —Cl | H | —CH$_3$ | H | 95.5 – 96 |
| 182 | —Cl | H | —C$_6$H$_5$ | H | 127 – 127.5 |
| 183 | —Cl | H | —CH$_3$ | —Cl | 176 – 176.5 |
| 184 | —Cl | H | —C$_6$H$_5$ | —Cl | 143.5 – 144 |
| 185 | H | —Cl | H | —Cl | 120.5 – 121 |
| 186 | H | —Cl | H | —OCH$_3$ | 106 – 106.5 |

EXAMPLE 3

A polyester fabric (for example "Dacron") is padded at room temperature (about 20° C) with an aqueous dispersion, which contains, per liter, 2 g of one of the compounds of the formulae (163) to (175) as well as 1 g of a product of the addition reaction of about 8 mols of ethylene oxide with 1 mol of p-tert.-octylphenol, and dried at about 100° C. The dry material is then subjected to a heat treatment at 160° to 220° C, the treatment time being 2 minutes down to a few seconds, depending on the temperature. The material treated in this way shows a strong brightening effect with good fastness to light.

What we claim is:

1. Process for the manufacture of styrene compounds of the formula

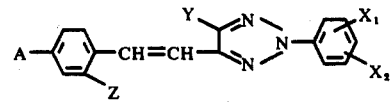

wherein A denotes one of the ring systems

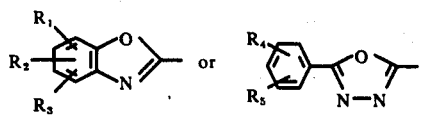 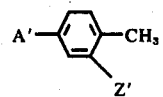

and wherein R₁ denotes hydrogen, alkyl with 1 to 8 carbon atoms, cyclohexyl, phenylalkyl with 1 to 3 carbon atoms in the alkyl part, phenyl, alkoxy with 1 to 4 carbon atoms, or chlorine, or, conjointly with R₂, denotes alkylene with 3 or 4 carbon atoms, R₂ denotes hydrogen or alkyl with 1 to 4 carbon atoms or, conjointly with R₁, denotes alkylene with 3 or 4 carbon atoms, R₃ denotes hydrogen or methyl, R₄ denotes hydrogen, m-methyl, alkyl with 2 to 8 carbon atoms, phenyl, alkoxy with 1 to 4 carbon atoms, or chlorine, or, conjointly with R₅, denotes a fused benzene ring, R₅ denotes hydrogen or chlorine or, conjointly with R₄, denotes a fused benzene ring, X₁ denotes hydrogen, alkyl with 2 to 4 carbon atoms, alkoxy with 1 to 4 carbon atoms or chlorine, X₂ denotes hydrogen or chlorine, Y denotes hydrogen, chlorine, alkyl with 1 to 4 carbon atoms or phenyl and Z denotes hydrogen or chlorine, which comprises reacting a methyl compound of the formula

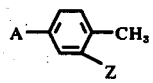

with a Schiff's base of the formula

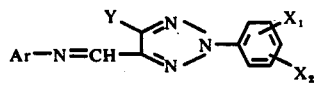

wherein Ar denotes an aromatic radical, in dimethylformamide in the presence of a strongly basic alkali metal compound, the reaction mixture being irradiated, at least initially, with UV light.

2. Process according to claim 1 for the manufacture of styrene compounds of the formula

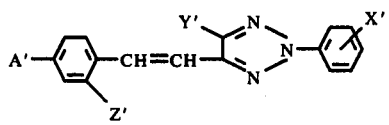

wherein A' denotes one of the ring systems

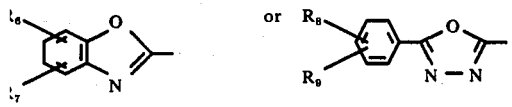

and wherein R₆ denotes hydrogen, alkyl with 1 to 4 carbon atoms, cyclohexyl, benzyl, α,α-dimethylbenzyl, methoxy, phenyl or chlorine, R₇ denotes hydrogen or methyl, R₈ denotes hydrogen, m-methyl, alkyl with 2 to 4 carbon atoms, phenyl, methoxy or chlorine or, conjointly with R₉, denotes a fused benzene ring, R₉ denotes hydrogen or, conjointly with R₈, denotes a fused benzene ring, X' denotes hydrogen, alkyl with 2 to 4 carbon atoms, methoxy or chlorine, Y' denotes hydrogen, methyl or phenyl and Z' denotes hydrogen or chlorine, which comprises reacting a methyl compound of the formula

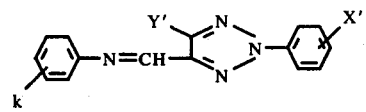

with a Schiff's base of the formula

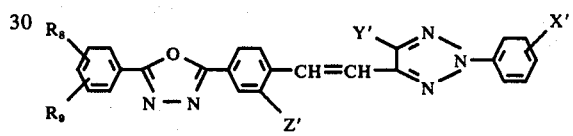

wherein k denotes hydrogen or chlorine, in dimethylformamide in the presence of an alkali metal compound of the formula $$MOC_{n-1}H_{2n-1}$$

wherein M represents potassium or sodium and n denotes an integer from 1 to 6, the reaction mixture initially being irradiated with UV light of wavelengths of above 300 nm.

3. Process according to claim 1 for the manufacture of styryl derivatives of the formula

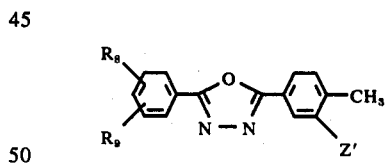

wherein R₈ denotes hydrogen, m-methyl, alkyl with 2 to 4 carbon atoms, phenyl, methoxy or chlorine, or, conjointly with R₉, denotes a fused benzene ring, R₉ denotes hydrogen or, conjointly with R₈, denotes a fused benzene ring, X' denotes hydrogen, alkyl with 2 to 4 carbon atoms, methoxy or chlorine, Y' denotes hydrogen, methyl or phenyl and Z' denotes hydrogen or chlorine, which comprises reacting a methyl compound of the formula

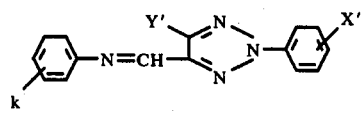

with a Schiff's base of the formula

wherein k denotes hydrogen or chlorine, in dimethylformamide in the presence of an alkali metal compound of the formula $$MOC_{n-1}H_{2n-1}$$

wherein M represents potassium or sodium and n denotes an integer from 1 to 6, the reaction mixture initially being irradiated with UV light of wavelengths of above 300 nm.

4. Process according to claim 1, wherein potassium hydroxide is used as the alkali metal compound and the reaction is carried out at a temperature of 10° to 40° C.

5. Styrene derivatives of the formula

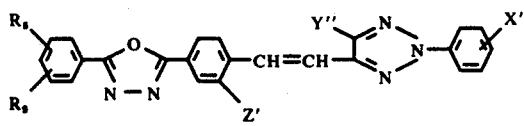

wherein $R_8$ denotes hydrogen, m-methyl, alkyl with 2 to 4 carbon atoms, phenyl, methoxy or chlorine, or, conjointly with $R_9$, denotes a fused benzene ring, $R_9$ denotes hydrogen or, conjointly with $R_8$, denotes a fused benzene ring, $X'$ denotes hydrogen, alkyl with 2 to 4 carbon atoms, methoxy or chlorine, $Y''$ denotes methyl or phenyl and $Z'$ denotes hydrogen or chlorine.

6. Styrene derivatives according to claim 5 of the formula

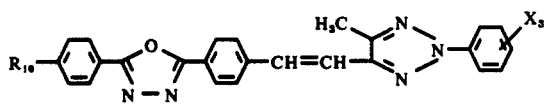

wherein $R_{10}$ denotes chlorine, methoxy, tert. butyl or phenyl and $X_3$ denotes hydrogen, chlorine or p-methoxy.

7. The styrene compound according to claim 5 of the formula

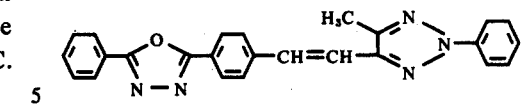

8. The styrene compound according to claim 5 of the formula

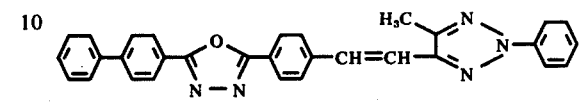

9. The styrene compound according to claim 5 of the formula

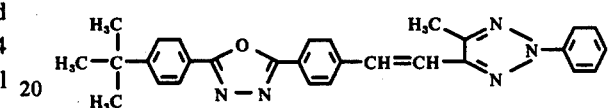

10. Process for the optical brightening of high molecular organic materials, which comprises incorporating into or applying to these materials a compound as defined in claim 5.

11. Process according to claim 10, wherein the brightener is incorporated into spinning melts of polyester and these melts are then spun.

12. Process according to claim 10, wherein polyester is treated according to the pad-bake method.

13. Process according to claim 10, wherein 0.001 to 2%, preferably 0.01 to 0.5%, of the brightener, relative to the weight of the material to be optically brightened, are applied to the materials to be brightened or are incorporated into these materials.

* * * * *